United States Patent
Matsushita et al.

(10) Patent No.: US 8,486,442 B2
(45) Date of Patent: Jul. 16, 2013

(54) EXTERNAL PATCH CONTAINING ESTROGEN AND/OR PROGESTOGEN

(75) Inventors: Kunihiko Matsushita, Kagawa (JP); Kenichi Hattori, Tokushima (JP); Masahiro Yamaji, Higashikagawa (JP)

(73) Assignees: Teikoku Seiyaku Co. Ltd., Higashikagawa-shi (JP); Fuso Pharmaceutical Industries Ltd., Osaka-shi (JP)

( * ) Notice: Subject to any disclaimer, the term of this patent is extended or adjusted under 35 U.S.C. 154(b) by 1553 days.

(21) Appl. No.: 10/556,851

(22) PCT Filed: May 13, 2004

(86) PCT No.: PCT/JP2004/006451
§ 371 (c)(1),
(2), (4) Date: Nov. 14, 2005

(87) PCT Pub. No.: WO2004/100959
PCT Pub. Date: Nov. 25, 2004

(65) Prior Publication Data
US 2007/0065493 A1    Mar. 22, 2007

(30) Foreign Application Priority Data
May 14, 2003    (JP) .................. 2003-136218

(51) Int. Cl.
*A61F 13/00*    (2006.01)
*A61L 15/00*    (2006.01)

(52) U.S. Cl.
USPC ........................ 424/448; 424/449; 424/445

(58) Field of Classification Search
None
See application file for complete search history.

(56) References Cited

U.S. PATENT DOCUMENTS

| | | | |
|---|---|---|---|
| 5,128,138 A * | 7/1992 | Blank | 424/449 |
| 5,200,190 A * | 4/1993 | Azuma et al. | 424/443 |
| 5,580,572 A | 12/1996 | Mikler et al. | |
| 5,602,015 A | 2/1997 | Sudhir | |
| 5,744,446 A | 4/1998 | Lollar et al. | |

(Continued)

FOREIGN PATENT DOCUMENTS

| EP | 0 822 255 A2 | 2/1998 |
|---|---|---|
| EP | 0976405 A1 | 2/2000 |

(Continued)

OTHER PUBLICATIONS

Batile et al., "Alloantibody from a Patient with Severe von Willebrand Disease Inhibits von Willebrand Factor-FVIII Interaction," *Ann. Hematol.* 75:111-115 (1997).

(Continued)

*Primary Examiner* — Anand Desai
*Assistant Examiner* — Melissa Mercier
(74) *Attorney, Agent, or Firm* — Ostrager Chong Flaherty & Broitman P.C.

(57) ABSTRACT

An external patch capable of stable prolonged release and transdermal absorption of active ingredient hormones (estrogens and/or progestogens) contained in a pressure sensitive adhesive layer, which external patch ensures low irritation on the skin. In particular, an external patch comprising a support and, superimposed thereon, a pressure sensitive adhesive layer, characterized in that the pressure sensitive adhesive layer comprises, as indispensable components, 5 to 50 wt. % of styrene/isoprene/styrene block copolymer, 20 to 70 wt. % of tackifier resin, 10 to 60 wt. % of softener and 1 to 20 wt. % of polyvinylpyrrolidone and contains, as an active ingredient, estrogen and/or progestogen.

13 Claims, 1 Drawing Sheet

—○— Example 3(a)
—●— Example 3(b)
—△— Comparative Example 1 (c)
—▲— Comparative Example 1 (d)

(a) Example 3 (stored at 25°C for 2 months)
(b) Example 3 (stored at 4°C for 2 months)
(c) Comparative Example 1 (stored at 25°C for 2 months)
(d) Comparative Example 1 (stored at 4°C for 2 months)

U.S. PATENT DOCUMENTS

| | | | |
|---|---|---|---|
| 6,210,675 B1 | 4/2001 | Highfield et al. | |
| 6,902,741 B1 * | 6/2005 | Grawe et al. | 424/448 |
| 7,067,313 B1 | 6/2006 | Jacquemin et al. | |
| 2003/0175268 A1 | 9/2003 | Saint-Remy et al. | |
| 2004/0039356 A1 * | 2/2004 | Maki et al. | 604/307 |

FOREIGN PATENT DOCUMENTS

| | | | |
|---|---|---|---|
| JP | 11-001441 | * | 4/1998 |
| JP | 11001441 | | 1/1999 |
| WO | WO 97/26010 A1 | | 7/1997 |
| WO | WO 01/04269 A1 | | 1/2001 |

OTHER PUBLICATIONS

Begany, "Monoclonal Antibody Improves Sepsis" *Pulmonary Reviews.Com* vol. 5, No. 8 (2000).

Cobb, "Septic Polyarthritis in a Hemophiliac," *J. Rheumatol.* 11:87-89 (1984).

Ferenz and Tozzi, "Sepsis due to an Infected Pseudocyst of Hemophilia," *Clin. Orthopaedics Rel. Res.* 244:254-257 (1989).

Freeman et al., "The Role of Inflammation in Sepsis and Septic Shock: A Meta-Analysis of Both Clinical and Preclinical Trials of Anti-Inflammatory Therapies," *Inflammation: Basic Principles and Clinical Correlates*, 3rd Ed., Lippincott Williams & Wilkins, Philadelphia, PA, pp. 965-975 (1999).

Gawryl and Hoyer, "Inactivation of Factor VIII Coagulant Activity by Two Different Types of Human Antibodies," *Blood* 60:1103-1109 (1982).

Gilles et al., "Anti-Factor VIII Antibodies of Hemophiliac Patients Are Frequently Directed Towards Nonfunctional Determinants and Do Not Exhibit Isotypic Restriction," *Blood* 82:2452-2461 (1993).

Gilles et al., "The Arg 2150 His Mutation Within the Factor VIII C1 Domain Eliminates a B Cell Epitope that is Present Only on Factor VIII-Von Willebrand Factor Complexes," *Blood* 92(Suppl. 1):710a, Abstract 2919 (1998).

Gilles and Saint-Remy, "Healthy Subjects Produce both Anti-Factor VIII and Specific Anti-Idiotypic Antibodies," *J. Clin. Invest.* 94:1496-1505 (1994).

Ingerslev et al., "Applications of Immunoperoxidase Techniques in Specificity Testing of Monoclonal Antibodies (Mabs) Against Von Willebrand Factor (vWf)," *Clin. Chem. Acta* 174:65-82 (1988).

Jacquemin et al., "Mechanism and Kinetics of Factor VIII Inactivation: Study with an IgG4 Monoclonal Antibody Derived from a Hemophilia A Patient with Inhibitor," *Blood* 92:496-506 (1998).

Jacquemin et al., "A Human Antibody Directed to the Factor VIII C1 Domain Inhibits Factor VIII Cofactor Activity and Binding to von Willebrand Factor," *Blood* 95:156-163 (2000).

Jacquemin et al., "Glycosylation of Type 2 Factor VIII Inhibitor Determines Its Maximum Level of FVIII Inhibition," *Blood* 102:163a (2003). Abstract Only.

Janeway et al., "The Interaction of the Antibody Molecule with Specific Antigen," *Immunobiology*, 3rd Ed., Garland Publishing, New York, NY, pp. 3:7-3:11 (1997).

Janeway et al., "Germinal Center B Cells Undergo V-Region Somatic Hypermutation, and Cells With Mutations that Improve Affinity for Antigen are Selected," *Immunobiology*, 6th Ed., Garland Science Publishing, New York, NY, pp. 379-381 (2005).

Kailas et al., "Epitope Specificity of Anti-FVIII Antibodies During Immune Tolerance Therapy With Factor VIII Preparation Containing von Willebrand Factor," *Thromb. Res.* 107:291-302 (2002).

Kato et al., "Activity Enhancement of a Lung Cancer-Associated Human Monoclonal Antibody HB4C5 by N-Deglycosylation," *Hum. Antibod. Hybridomas* 4:9-14 (1993).

Khurana et al., "The Variable Domain Glycosylation in a Monoclonal Antibody Specific to GnRH Modulates Antigen Binding," *Biochem. Biophys. Res. Comm.* 234:465-469 (1997).

Lenting et al., "Identification of a Binding Site for Blood Coagulation Factor IXa on the Light Chain of Human Factor VIII," *J. Biol. Chem.* 269:7150-7155 (1994).

Ly et al., "Characterization of an Antibody to Factor VIII in a Patient with Acquired Hemophilia with Circulating Immune Complexes," *Scand. J. Haematol.* 28:132-140 (1982).

Martinell et al., "Peritonitis and Septic Shock—An Evaluation of Two Experimental Models in the Rat," *Eur. Surg. Res.* 17(3):160-166 (1985). Abstract only.

Merck Manual of Diagnosis and Disease, $17^{th}$ Ed., Beers et al. (Eds.), Merck Research Laboratories, Whitehouse, NJ, pp. 1143-1147 (1999).

Near et al., "Characterization of an Anti-Digoxin Antibody Binding Site by Site-Directed In Vitro Mutagenesis," *Mol. Immunol.* 30(4):369-377 (1993).

Peerlinck et al., "Antifactor VIII Antibody Inhibiting Allogeneic but not Autologous Factor VIII in Patients with Mild Hemophilia A," *Blood* 93:2267-2273 (1999).

Price et al., "Tissue Factor and Tissue Factor Pathway Inhibitor," *Anaesthesia* 59:483-492 (2004).

Riedemann and Ward, "Anti-Inflammatory Strategies for the Treatment of Sepsis," *Expert Opin. Biol. Ther.* 3(2):339-350 (2003).

Rudikoff et al., "Single Amino Acid Substitution Altering Antigen-Binding Specificity," *Proc. Natl. Acad. Sci. USA* 79:1979-1983 (1982).

Saint-Remy, "B- and T-cell Tolerance: From Basic Concepts to Clinical Practice." *Haematologica* 85(Suppl. to No. 10):93-96 (2000).

Sato et al., "Humanization of an Anti-Human IL-6 Mouse Monoclonal Antibody Glycosylated in Its Heavy Chain Variable Region," *Hum. Antibod. Hybridomas* 7(4):175-183 (1996).

Scandella et al., "Localization of Epitopes for Human Factor VIII Inhibitor Antibodies by Immunoblotting and Antibody Neutralization," *Blood* 74:1618-1626 (1989).

Singh et al., "Antithrombotic Effects of Controlled Inhibition of Factor VIII with a Partially Inhibitory Human Monoclonal Antibody in a Murine Vena Cava Thrombosis Model," *Blood* 99:3235-3240 (2002).

Taylor et al., "7E3 F(ab')2 , a Monoclonal Antibody to the Platelet GPIIb/IIIa Receptor, Protects Against Microangiopathic Hemolytic Anemia and Microvascular Thrombotic Renal Failure in Baboons Treated With C4B Binding Protein and a Sublethal Infusion of *Escherichia coli*," *Blood* 89:4078-4084 (1997).

Wright et al., "Antibody Variable Region Glycosylation: Position Effects on Antigen Binding and Carbohydrate Structure," *EMBO J.* 10:2717-2723 (1991).

Yan et al., "Therapeutic Effects of Lysophosphatidylcholine in Experimental Sepsis," *Nature Medicine* 10:161-167 (2004).

Yelton et al., "Affinity Maturation of the BR96 Anti-Carcinoma Antibody by Codon-Based Mutagenesis," *J. Immunol.* 155:1994-2004 (1995).

Ziegler et al., "Treatment of Gram-Negative Bacteremia and Septic Shock with HA-1A Human Monoclonal Antibody Against Endotoxin. A Randomized, Double-Blind, Placebo-Controlled Trial. The HA-1A Sepsis Study Group," *New Engl. J. Med.* 324:429-436 (1991). Abstract only.

Written Opinion for PCT/BE2004/000118 mailed Feb. 2, 2005.

International Search Report for PCT/BE2004/000118 mailed Feb. 2, 2005.

International Preliminary Report on Patentability for PCT/BE2004/000118 dated Dec. 2, 2005.

* cited by examiner (a) Example 3 (stored at 25°C for 2 months)
(b) Example 3 (stored at 4°C for 2 months)
(c) Comparative Example 1 (stored at 25°C for 2 months)
(d) Comparative Example 1 (stored at 4°C for 2 months)

(a) Example 3 (stored at 25°C for 2 months)
(b) Example 3 (stored at 60°C for 2 months)
(c) Comparative Example 2 (stored at 25°C for 2 months)
(d) Comparative Example 2 (stored at 60°C for 2 months)

EXTERNAL PATCH CONTAINING ESTROGEN AND/OR PROGESTOGEN

The present application is an English language translation of International Application No. PCT/JP2004/006451, filed on May 13, 2004, which claims priority to Japanese Application No. JP 2003-136218, filed on May 14, 2003; both applications are hereby incorporated by reference.

TECHNICAL FIELD

The present invention relates to an external patch containing estrogen and/or progestogen that are useful for prevention or treatment of diseases such as menopausal syndrome (e.g., headaches, hot flushes, sweating, etc.) which often occurs in climacteric or postmenopausal women, osteoporosis, Alzheimer's disease, arteriosclerosis, hyperlipemia, and other diseases.

More specifically, the present invention relates to a transdermal patch that uses an adhesive base comprising as effective components a styrene-isoprene-styrene block copolymer (SIS), an adhesive resin, a softener, and polyvinylpyrrolidone (PVP) and in which the adhesive layer contains as active ingredients hormones estrogen and/or progestogen.

BACKGROUND ART

Postmenopausal women experience a rapid loss of ovary function. The associated loss of estrogen often brings about heat sensation, hot flushes, sweating, and other vasomotor symptoms, which are major complaints of menopausal syndrome. The reduced secretion of the hormone is also considered to cause cardiovascular disorders and osteoporosis. In order to prevent or treat these symptoms, oral preparations and injections of estrogen are given to women suffering from menopausal syndrome. The oral administration, however, results in much of the drug being metabolized in the digestive tract and liver and thus requires a high dose to achieve the desired effect. The administration by injection not only accompanies pain caused by the needle, but also causes the blood estrogen level to increase rapidly. Moreover, the efficacy of the drug diminishes in a short period of time. When administered via these administration routes, estrogen may cause thrombosis, endometriosis, uterine cancer, and other side effects. For these reasons, it is necessary to find a way to maintain the drug level in the body at the minimum required level for an extended period of time.

One way to provide sustained drug release is via a transdermal absorption preparation. Since administration via this route is different from administration via digestive tract or liver and transdermal absorption preparations are easy to handle, this route of administration has drawn much attention and several attempts have been made to date to provide ideal transdermal absorption preparations.

One example is a reservoir-type preparation in which estradiol is dissolved in a gel made of hydroxypropyl cellulose and ethanol. This reservoir-type preparation controls the release of estradiol by the use of an ethylene-vinyl acetate film (Japanese Patent Laid-Open Publication No. Sho 57-154122). However, since these preparations contain a volatile ingredient, there is a fear that drug releasability is changed. In addition, contained ethanol is irritant to the skin, frequently causing rubor where the preparation is applied to the skin.

Another proposed example is a transdermal absorption preparation containing complex estrogen (Japanese Patent Laid-Open Publication No. Sho 60-152413). This preparation also contains menthol as a transdermal absorption enhancer. The problem of this preparation is that volatile menthol evaporates during storage or use, so that the rate of drug release changes over time.

Still another transdermal absorption preparation uses an acrylic adhesive in the adhesive layer (Japanese Patent Laid-Open Publications No. Hei 4-342532 and Hei 8-27003). The preparation contains as active components norethisterone, estradiol, and esters thereof. The acrylic adhesive used in this preparation has a low ability to release the drug and is irritant to the skin. The acrylic adhesive is thus unsuitable for transdermal absorption preparations for the purpose of continuous application over an extended period of time. Another estrogen-containing transdermal absorption patch using styrene-isoprene-styrene block copolymer (SIS) is proposed in which a fatty acid ester is used to serve as a component to dissolve estrogen (Japanese Patent Laid-Open Publications No. Hei 5-148145). The fatty acid ester used in this preparation not only decreases the cohesion of the adhesive, resulting in the adhesive remaining where it is applied, but is also irritant to the skin.

The skin tissue of a living body serves as a defense function to prevent the entrance of foreign substances into the living body. Thus, delivering effective doses of a drug through the skin is generally considered difficult. To overcome this problem, absorption enhancers are added to transdermal preparations. The addition of these enhancers in many cases increases the irritation to the skin, however.

The external preparation used in hormone replacement therapies must be left on the skin for a prolonged period of time to maintain the effective blood level of a drug. In order to allow the external preparation to be applied for a long period of time, it is necessary to improve the adhesive strength of a base material of the external preparation. In addition, it is particularly necessary to enhance the anchor effect of an adhesive on the irregularities of the skin surface in order to increase a holding power. To enhance the anchor effect of the adhesive on the irregularities of the skin surface, the activity of the polymer to serve as the adhesive base material must be increased. This, however, decreases the cohesive strength of the adhesive, which leads to occurrences of cohesive fractures and results in the adhesive remaining on the skin upon peeling-off of the external preparation. Thus, long-term application of the external preparation requires control over the anchor effect of the adhesive and its cohesive strength.

Many articles now suggest that the flexibility of a backing used in the external patches is a key factor in achieving high transdermal drug absorption. While such a flexible backing having physical properties adequate for such a purpose may be made of different materials such as low-density polymer films, nonwoven fabrics, and woven fabrics, each requires a substantial free volume to ensure the flexibility of the backing. However, a backing having a large free volume tends to adsorb much drug and, as a result, the rate of the drug release decreases after a long-term storage period, resulting in insufficient performance of the external patch.

In view of the aforementioned problems, it is an object of the present invention to provide an external patch that can ensure high transdermal absorption of estrogen and/or progestogen and have little irritancy to the skin.

DISCLOSURE OF THE INVENTION

The present inventors have conducted extensive researches to solve the above-described problems and have discovered that an external patch with an adhesive layer having a particular composition offers a solution to all of the problems described above. Specifically, the adhesive layer contains as essential components astyrene-isoprene-styreneblockcopolymer (SIS), an adhesive resin, a softener, a polyvinylpyrrolidone (PVP), and estrogen and/or progestogen.

The present invention thus provides an external patch comprising a backing and an adhesive layer laminated onto the backing, the adhesive layer containing as essential components a 5 to 50 wt % styrene-isoprene-styrene block copolymer (SIS), a 20 to 70 wt % adhesive resin, a 10 to 60 wt % softener and a 1 to 20 wt % polyvinylpyrrolidone (PVP), along with estrogen and/or progestogen as active ingredients.

As described above, one feature of the present invention is that the adhesive base material of the external patch contains, along with the SIS, the adhesive resin, and the PVP, the softener for dissolving estrogen and/or progestogen and improving the following ability of the patch with the irregularities of the skin surface. The crystallization of the drug in the patch base material is thus reduced in the external patch of the present invention. Furthermore, the external patch ensures stable drug release and causes little irritancy to the skin. These are also other characteristic features of the external patch of the present invention.

BEST MODE FOR CARRYING OUT THE INVENTION

Figure 1:
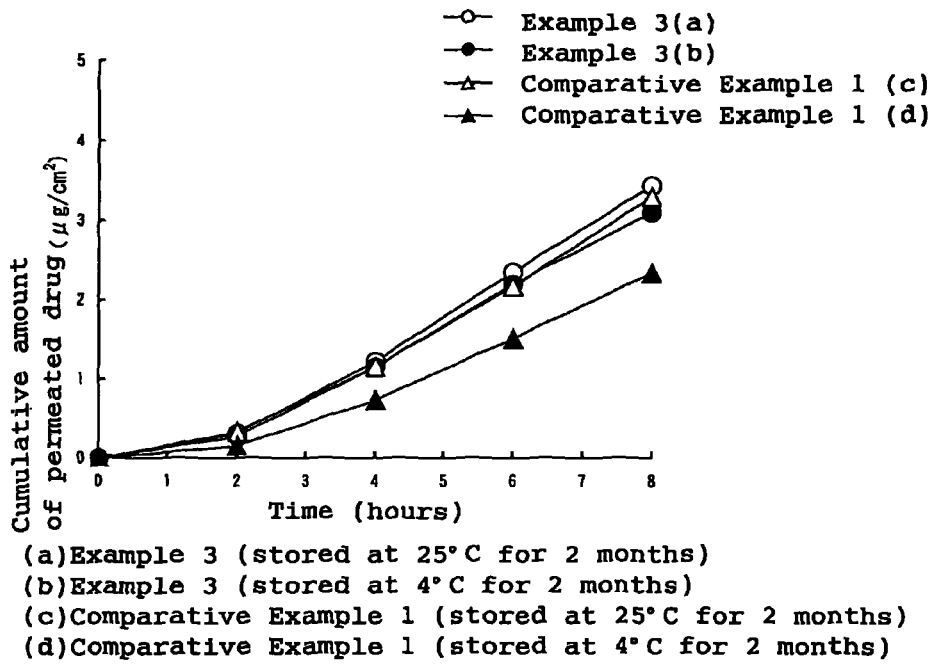
FIG. 1 is a graph showing the results of an in vitro rat permeability test conducted in Test Example 2.

In the external patch of the present invention, the SIS is used in the adhesive base material in an amount of preferably 5 to 50 wt %, and more preferably 10 to 30 wt %. If this amount is less than 5 wt %, then the cohesive strength of the base material is decreased and the base material may thus remain on the skin surface. If this amount is greater than 50 wt %, then the cohesive strength of the base material becomes excessively high, so that the adhesion of the base material may be decreased or the mixing of the base material may become difficult.

The adhesive resin used with the SIS serves to make the base adhesive by being mixed with the SIS. While the adhesive resin may be such a resin as rosin-based resin, oil-based resin, and terpene resin, the rosin-based resins are particularly preferred for use in the present invention. Examples of the rosin-based resin include rosin esters, hydrogenated rosins, rosin glycerides, hydrogenated rosin glycerides, rosin acid, and rosin polymers. Of these, hydrogenated rosin glycerides are particularly preferred.

The rosin-based resins can dissolve more progestogen than other types of adhesive resins and can thus effectively prevent crystallization of the drug in the preparation. The amount of the rosin-based resin is preferably 7 times or more, and more preferably 10 times or more of the amount of progestogen. To ensure favorable adhesion of the patch, the amount of the rosin-based resin in the preparation is preferably in the range of 20 to 70 wt %, and more preferably in the range of 40 to 50 wt %. If this amount is less than 20 wt %, then the patch loses adhesion. If present in amounts greater than 70 wt %, the rosin-based resin may make the patch too sticky to peel it off from the skin without causing skin irritation.

The softener is added to soften the adhesive and thereby improve the following ability of the adhesive with the skin. It is also intended to adjust the adhesion of the adhesive, thereby reducing the skin irritation upon removal of the patch. Examples of the softener include paraffin-based oils, silicone oils, higher fatty acids, vegetable oils, and polybutenes. Of these, liquid paraffins are particularly preferred. The amount of the softener is typically in the range of 10 to 60 wt %, and preferably in the range of 20 to 40 wt %. If this amount is less than 10 wt %, then the following property of the adhesive with the skin is reduced and the patch may come off the skin easily. If this amount is greater than 60 wt %, then the cohesive strength of the adhesive is decreased, so that the glue may remain where the patch is applied.

The PVP used in the adhesive layer serves as a component in which to dissolve estrogen. While the PVP for use in the present invention may be of any molecular weight, it preferably has a molecular weight of 1,000,000 or less. The amount of PVP is preferably twice or more, and more preferably 5 times the amount of estrogen. The amount of PVP in the preparation is preferably in the range of 1 to 20 wt %, and more preferably in the range of 2 to 10 wt %. The PVP, if present in amounts less than 1wt %, cannot dissolve sufficient amounts of estrogen. As a result, estrogen may crystallize during storage if it is present in excessive amounts or estrogen may not be released in sufficient amounts to maintain the effective blood hormone level if added in less amounts than are required to form crystals. If present in amounts greater than 20 wt %, the PVP causes a decrease in the cohesive strength of the base material and the glue may remain where the patch is applied.

According to the present invention, estrogen is typically used in an amount of 0.5 to 5 wt %, and preferably in an amount of 1 to 3 wt %. Progestogen is typically used in an amount of 1 to 10 wt %, and preferably in an amount of 2 to 5 wt %.

Aside from the above-described components, the patch provided in accordance with the present invention may contain other components commonly used in the production of patch preparations and properly selected to suit the desired purpose. Examples of such a component include antioxidants, such as dibutylhydroxytoluene (BHT), and fillers, such as titanium oxide and silicon dioxide.

While the adhesive layer in the patch of the present invention may have any thickness, it is preferably about 50 to about 100 μm thick. Too thin a layer has a decreased adhesion, whereas too thick a layer carries an increased amount of drug that is left unused, leading to an increase in the production cost. In addition, too thick a layer can easily come off when rubbed against clothes.

The flexibility and stretchability of the backing used in the external patch of the present invention have proven to affect how closely the patch will follow the skin and have turned out to be important factors in achieving high transdermal drug absorption. While the highly flexible and highly stretchable backing may be made of different materials such as low-density polymer films, nonwoven fabrics, and woven fabrics, the amount of the drug adsorbed by the backing increases as the free volume of the backing is increased to ensure its flexibility and stretchability. Thus, a backing with a large free volume causes a reduction over time in the rate of the drug release from the patch. As a result, the performance of the external patch may become insufficient.

To address this problem, the present inventors devised a backing that is a laminate of a very thin, dense drug non-adsorptive layer and a flexible film that can closely follow the irregularities of the skin surface as well as the movement of the skin. This backing has turned out to not adsorb the drug and ensure high transdermal drug absorption. Preferably, the drug non-adsorptive layer is made of a material that has a dense structure, can form thin film, and does not interact with the drug. Examples of such materials include metal films, metal-deposited films, and high density polymer films. Of these materials, high density polymer films are preferred because of their versatility and cost efficiency. A particularly preferred material is polyethyleneterephthalate film. The film is preferably 0.1 to 20 μm thick. The polyethylene terephthalate film thicker than 20 μm is too stiff to closely follow the irregularities of the skin surface or the movement of the skin, resulting in a decreased transdermal drug absorption.

The flexible film laminated to the drug non-adsorptive layer may be any flexible film that can closely follow the irregularities of the skin surface as well as the movement of the skin. Examples include woven fabrics, nonwoven fabrics, and polymer films made of polymer materials such as polyethylene, polypropylene, polyurea, polyurethane, polyester, polyvinyl alcohol, and polyvinylchloride. These films are typically 1 to 200 μm thick, and preferably 20 to 100 μm thick. The film thinner than 1 μm is not rigid enough and is thus difficult to handle, whereas the film thicker than 200 μm cannot closely follow the irregularities of the skin surface or the movement of the skin, leading to a decrease in the transdermal drug absorption. Thick films tend to have the edges catch on clothes and come off the skin.

In the patch provided according to the present invention, a release liner is laminated to the adhesive layer. Such release liners are made of materials such as polyethylene terephthalate, polypropylene, and paper. If necessary, the release liner may be silicone-treated so that it can be peeled with appropriate force.

The external patch of the present invention can be manufactured in the following manner. The SIS, the softener, the adhesive agent, the antioxidant, the filler, and other components are dissolved in an appropriate volume of toluene. The hormone and PVP, the major ingredients, are dissolved in an appropriate volume of N-methyl-2-pyrrolidone and the resulting solution is mixed with the adhesive solution. After degassing treatment, the mixture is applied to a silicone-treated polyethylene terephthalate film, and the coating is dried at 100° C. for 10 min to form a 50 to 100 μm thick adhesive layer. The adhesive layer is laminated with the backing, which is a laminate of a polyethylene terephthalate film and a low density-polyethylene film, with the polyethylene terephthalate side facing the adhesive layer. The resulting laminate is cut into a desired size and shape to make the transdermal absorption preparation of the present invention.

The external patch so produced is advantageous in that the active ingredients estrogen and/or progestogen are well dissolved in the adhesive layer and are not adsorbed by the backing, and the patch can closely follow the irregularities of the skin surface or the movement of the skin. The patch ensures high transdermal absorption of the active ingredients and can remain effective in extended use. Thus, the patch of the present invention is useful in the prevention and treatment of climacteric or menopausal syndrome, including headache, hot flushes and sweating, osteoporosis, Alzheimer's disease, arterial sclerosis, hyperlipidemia, and other diseases.

EXAMPLES

The present invention will now be described with reference to examples, which is not intended to limit the scope of the invention in anyway. Unless otherwise specified, the compositions of Examples and Comparative Examples are given in percentages by weight.

Examples 1 through 4

According to the formulae shown in Table 1 below, external patches of the present invention of respective Examples were prepared.

TABLE 1

| Composition | Examples | | | |
| --- | --- | --- | --- | --- |
|  | 1 | 2 | 3 | 4 |
| SIS | 30 | 10 | 15 | 10 |
| Rosin-based resin | 30 | 40 | 50 | 50 |
| Polybutene | 0 | 10 | 10 | 0 |
| Liquid paraffin | 32.5 | 31 | 15 | 26 |
| BHT | 1 | 1 | 1 | 1 |
| PVP | 3 | 3 | 3 | 6 |
| Estradiol | 0.5 | 1 | 1 | 2 |
| Norethisterone acetate | 3 | 4 | 5 | 5 |

Comparative Examples 1 through 4

According to the formulae shown in Table 2 below, external patches of the present invention of respective Comparative Examples were prepared.

TABLE 2

| Composition | Comparative Examples | | | |
| --- | --- | --- | --- | --- |
|  | 1 | 2 | 3 | 4 |
| SIS | 15 | 15 | 15 | 15 |
| Rosin-based resin | 50 | 15 | 40 | 15 |
| Polybutene | 0 | 15 | 0 | 15 |
| Liquid paraffin | 28 | 45 | 37 | 42 |
| BHT | 1 | 1 | 1 | 1 |
| PVP | 0 | 3 | 0 | 3 |
| Estradiol | 1 | 1 | 3 | 1 |
| Norethisterone acetate | 5 | 5 | 4 | 8 |

Test Example 1

Each of the hormone preparations of Examples 1 through 4 and Comparative Examples 1 through 4 were cut into a 10 cm² square sheet. Each sheet was packaged in an aluminum-laminated envelope. The aluminum-laminated envelopes were stored under different temperature conditions and were observed over time both visually and with a microscope (magnification=×400) to see if crystals had formed in the adhesive layer. The results are shown in Table 3 below.

TABLE 3

| Samples | 4° C. | | 25° C. | | 40° C. | | 60° C. | |
| --- | --- | --- | --- | --- | --- | --- | --- | --- |
|  | 1 month | 2 months | 1 month | 2 months | 1 month | 2 months | 1 month | 2 months |
| Example 1 | — | — | — | — | — | — | — | — |
| Example 2 | — | — | — | — | — | — | — | — |
| Example 3 | — | — | — | — | — | — | — | — |
| Example 4 | — | — | — | — | — | — | — | — |

TABLE 3-continued

| Samples | 4° C. | | 25° C. | | 40° C. | | 60° C. | |
|---|---|---|---|---|---|---|---|---|
| | 1 month | 2 months | 1 month | 2 months | 1 month | 2 months | 1 month | 2 months |
| Comparative Example 1 | — | ● | — | ● | — | — | — | — |
| Comparative Example 2 | — | — | — | — | — | ● | ● | ●○ |
| Comparative Example 3 | ● | ●○ | — | — | — | — | — | — |
| Comparative Example 4 | — | — | — | ● | ● | ●○ | ●○ | ●○ |

Note:
A dash signifies that no crystallization was observed under microscopy or visual inspection.

A solid circle signifies that crystallization was observed by microscopy.

A blank circle signifies that crystallization was observed visually.

As can be seen from the results above, no crystallization was observed in the adhesive layer in any of the patches of Examples 1 through 4 at any of the temperatures tested. In contrast, crystallization was observed in the adhesive layers of the patches of Comparative Examples 1 and 3 during storage at 4° C. while no crystals were formed in these patches during storage at 40° C. and 60° C. In the patch of Comparative Example 2, crystals were formed in the adhesive layer during storage at 40° C. and 60° C., but not at 4° C. and 25° C. In the patch of Comparative Example 4, crystals were formed in the adhesive layer during storage at 25° C., 40° C. and 60° C., but not at 4° C.

Test Example 2

The ability of the patch of the present invention to release estradiol was examined in an in vitro rat skin permeability test using the sample patches of Example 3 and Comparative Example 1. Two patches of each example were used after stored at 4° C. and 25° C. for 2 months. Specifically, shaved abdominal skin of rats was mounted on a Franz cell with the receiving chamber filled with phosphate buffered saline and a hot water having a temperature of 37° C. was circulated through the water jacket. A circular piece (1.77 cm²) stamped out of each of the patches of Example 3 and Comparative Example 1 was applied to the rat skin. The receptor solution was sampled at intervals and the amount of estradiol permeated into each sample solution was determined by liquid chromatography.

The results are shown in FIG. 1.

As shown, no significant difference in the drug permeability was observed between the patches of Example 3 stored at 4° C. and 25° C. for 2 months. The patch of Comparative Example 1 stored at 4° C. for 2 months became less permeable as compared to the patch of Comparative Example 1 stored at 25° C. (for 2 months).

Test Example 3

Figure 2:
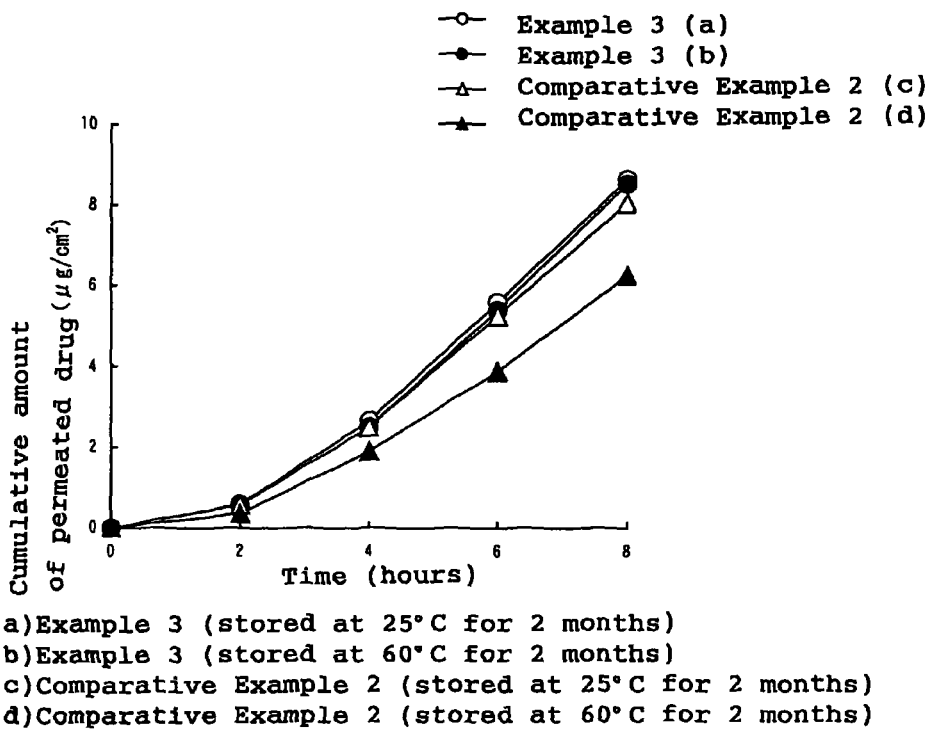
FIG. 2 is a graph showing the results of an in vitro rat permeability test conducted in Test Example 3.

The ability of the patch of the present invention to release norethisterone was examined in an in vitro rat skin permeability test using the sample patches of Example 3 and Comparative Example 2. Two patches of each example were used after stored at 25° C. and 60° C. for 2 months. The test was conducted in the same manner as in Test Example 2 to determine estradiol releaseability. The results are shown in FIG. 2.

As shown, no significant difference in the drug permeability was observed between the patches of Example 3 stored at 25° C. and 60° C. for 2 months. The patch of Comparative Example 2 stored at 60° C. for 2 months became less permeable as compared to the patch of Comparative Example 2 stored at 25° C. for 2 months.

Test Example 4

A primary irritation test was conducted using rabbit skin. In the test, a comparison was made between the patch of Example 3, a commercial product A (control, a hormone-containing tape preparation using an acrylic adhesive) and a commercial product B (control, a reservoir-type patch in which the hormone is dissolved in ethanol). Each patch was applied to the shaved back skin of rabbits for 24 hours, and the skin was observed 1 hour and 24 hours after the removal of the patch. Each patch was applied to a group of five rabbits.

The results are shown in Table 4 below.

TABLE 4

| Sample | 1 hour after removal | 24 hours after removal |
|---|---|---|
| Example 3 | Minor erythema | Almost no irritancy symptoms observed |
| Commercial Product A | Erythema and minor edema in some animals | Minor erythema remained |
| Commercial Product B | Erythema and edema in all animals | Erythema remained |

As can be seen from the results above, the patches of Example 3 were significantly less irritant than the commercial products A and B.

INDUSTRIAL APPLICABILITY

As set forth, the patch provided in accordance with the present invention includes an adhesive layer that contains as essential components a styrene-isoprene-styrene block copolymer (SIS), an adhesive resin, a softener and a polyvinylpyrrolidone (PVP), along with an estrogen and/or a progestogen as active ingredients. The patch can retain much drug in its solvent and ensure stability of the drug. In the patch of the present invention, crystallization of the drug hardly occurs in the base material of the patch. As a result, the patch can ensure stable drug release and transdermal drug absorption. The patch of the present invention is also less irritant to the skin.

In addition, the patch of the present invention employs a laminate of a drug non-adsorptive layer and a flexible film to serve as the backing. This constructional lows the patch to closely follow the rough skin surface as well as the movement of the skin. Thus, the patch can ensure stable drug absorption through the skin during extended use.

The invention claimed is:

1. An external patch comprising a backing and an adhesive layer laminated onto the backing, the adhesive layer consisting of a) 5 to 50 wt % styrene-isoprene-styrene block copolymer (SIS);
b) 20 to 70 wt % rosin-based resin;
c) 10 to 60 wt % softener consisting of polybutene and/or liquid paraffin;
d) 1 to 20 wt % polyvinylpyrrolidone, as a dissolving component; and
e) an active ingredient selected from the group consisting of estrogen, progestogen or a combination of estrogen and progestogen, wherein the adhesive layer is free from any alcohol.

2. The patch according to claim 1, wherein the estrogen is 17-β-estradiol.

3. The patch according to claim 1, wherein the progestogen is norethisterone acetate.

4. The patch according to claim 1, wherein the backing is a laminate comprising a 0.1 to 20 μm thick polyethylene terephthalate film and a 1 to 200 μm thick flexible polymer film, nonwoven fabric or woven fabric.

5. An external patch comprising a backing and an adhesive layer laminated onto the backing, the adhesive layer consisting of
a) 5 to 50 wt % styrene-isoprene-styrene block copolymer (SIS);
b) 20 to 70 wt % rosin-based adhesive resin;
c) 10 to 60 wt % softener consisting of polybutene and/or liquid paraffin;
d) 1 to 20 wt % polyvinylpyrrolidone, as a dissolving component; and
e) an active ingredient selected from the group consisting of estrogen, progestogen or a combination of estrogen and progestogen, the adhesive layer being free from any alcohol.

6. The patch according to claim 5, wherein the estrogen is 17-β-estradiol.

7. The patch according to claim 5, wherein the progestogen is norethisterone acetate.

8. The patch according to claim 5, wherein the backing is a laminate comprising a 0.1 to 20 μm thick polyethylene terephthalate film and a 1 to 200 μm thick flexible polymer film, nonwoven fabric or woven fabric.

9. An external patch comprising a backing and an adhesive layer laminated onto the backing, the adhesive layer being free from any alcohol and consisting of
a) 10 to 30 wt % styrene-isoprene-styrene block copolymer (SIS);
b) 40 to 50 wt % rosin-based resin;
c) 20 to 40 wt % softener consisting of polybutene and/or liquid paraffin;
d) 2 to 10 wt % polyvinylpyrrolidone, as a dissolving component; and
e) 1 to 3 wt % estrogen or 2 to 5 wt % progestogen.

10. The patch according to claim 9, wherein the estrogen is 17-β-estradiol.

11. The patch according to claim 9, wherein the progestogen is norethisterone acetate.

12. The patch according to claim 9, wherein the backing is a laminate comprising a 0.1 to 20 μm thick polyethylene terephthalate film and a 1 to 200 μm thick flexible polymer film, nonwoven fabric or woven fabric.

13. An external patch comprising a backing and an adhesive layer laminated onto the backing, the adhesive layer being free from any alcohol and the adhesive layer consisting of a 5 to 50 wt % styrene-isoprene-styrene block copolymer (SIS), a 20 to 70 wt % rosin-based resin, a 10 to 60 wt % softener consisting of polybutene and/or liquid paraffin, and a 1 to 20 wt % polyvinylpyrrolidone, as a dissolving component, along with estrogen as an active ingredient, wherein the amount polyvinylpyrrolidone is at least 5 times or more the amount of estrogen.

* * * * *